(12) United States Patent
Turner et al.

(10) Patent No.: US 12,138,145 B2
(45) Date of Patent: Nov. 12, 2024

(54) ABSORBENT ARTICLE COMPRISING AN ADHESIVE COMPOSITION

(71) Applicant: The Procter & Gamble Company, Cincinnati, OH (US)

(72) Inventors: Robert Haines Turner, Cincinnati, OH (US); Torsten Lindner, Kronberg (DE); Matthias Morand, Bad Soden (DE); Benjamin John Kutay, Cincinnati, OH (US); Holger Beruda, Schwalbach (DE); Ekaterina Ponomarenko, Mechernich (DE); William L. Bunnelle, Ham Lake, MN (US); Jon Fagerness, Coon Rapids, MN (US); Nick Fowler, Odessa, TX (US); Bill Turner, Odessa, TX (US); Andres Sustic, Odessa, TX (US); Enrico Buenacosa, Odessa, TX (US); Steve Oetting, Odessa, TX (US); Steve McHaney, Odessa, TX (US); J. J. DeCair, Odessa, TX (US)

(73) Assignee: The Procter & Gamble Company, Cincinnati, OH (US)

( * ) Notice: Subject to any disclaimer, the term of this patent is extended or adjusted under 35 U.S.C. 154(b) by 19 days.

(21) Appl. No.: 17/901,907

(22) Filed: Sep. 2, 2022

(65) Prior Publication Data

US 2022/0409447 A1  Dec. 29, 2022

Related U.S. Application Data

(63) Continuation of application No. 16/387,712, filed on Apr. 18, 2019, now abandoned.
(Continued)

(51) Int. Cl.
*A61F 13/15* (2006.01)
*A61F 13/511* (2006.01)
(Continued)

(52) U.S. Cl.
CPC ...... *A61F 13/515* (2013.01); *A61F 13/51121* (2013.01); *A61F 13/51401* (2013.01);
(Continued)

(58) Field of Classification Search
CPC .............. A61F 13/515; A61F 13/51121; A61F 13/51401; A61F 13/539; A61F 2013/1591;
(Continued)

(56) References Cited

U.S. PATENT DOCUMENTS 3,338,992 A   8/1967 Allison
3,341,394 A   9/1967 Allison
(Continued)

FOREIGN PATENT DOCUMENTS

EP   0335484 A1   10/1989
WO   9516746 A1   6/1995
(Continued)

OTHER PUBLICATIONS

All Office Actions, U.S. Appl. No. 16/387,662, filed on Apr. 18, 2019.
All Office Actions, U.S. Appl. No. 16/387,675, filed on Apr. 18, 2019.
(Continued)

*Primary Examiner* — Jacqueline F Stephens
(74) *Attorney, Agent, or Firm* — Anna E. Haller; Angela K. Haughey; Richard L. Alexander (57) ABSTRACT

Described herein is an absorbent article. The absorbent article includes an assembly of components and an adhesive composition joining at least two of the assembly of components together. The adhesive composition includes from about 50 wt. % to about 80 wt. % of one or more copolymers
(Continued)

and a blend of one or more heterophase copolymers. The one or more copolymers include from about 30 mole % to about 70 mole % of monomer units selected from ethylene, 1-butene, and mixtures thereof. The one or more copolymers also include from about 30 mole % to about 70 mole % of propene monomer units. The adhesive composition is free of polyisobutylene and has a viscosity of from about 2,000 mPa·s to about 11,500 mPa·s at 150° C.

20 Claims, 1 Drawing Sheet

Related U.S. Application Data (60) Provisional application No. 62/660,359, filed on Apr. 20, 2018.

(51) Int. Cl.
  A61F 13/514 (2006.01)
  A61F 13/515 (2006.01)
  A61F 13/539 (2006.01)
  C08F 210/06 (2006.01)
  C08F 210/08 (2006.01)
  C09J 4/06 (2006.01)

(52) U.S. Cl.
  CPC .......... *A61F 13/539* (2013.01); *C08F 210/06* (2013.01); *C08F 210/08* (2013.01); *C09J 4/06* (2013.01); *A61F 2013/1591* (2013.01); *A61F 2013/51452* (2013.01); *A61F 2013/53908* (2013.01); *C08F 2800/10* (2013.01); *C09J 2301/414* (2020.08); *C09J 2400/263* (2013.01); *C09J 2423/10* (2013.01)

(58) Field of Classification Search
  CPC ............ A61F 2013/51452; A61F 2013/53908; C08F 210/06; C08F 210/08; C08F 2800/10; C09J 2301/414; C09J 2400/263; C09J 2423/10
  See application file for complete search history.

(56) References Cited

U.S. PATENT DOCUMENTS

| | | |
|---|---|---|
| 3,502,538 A | 3/1970 | Petersen |
| 3,502,763 A | 3/1970 | Hartmann |
| 3,542,615 A | 11/1970 | Dobo |
| 3,692,618 A | 9/1972 | Dorschner |
| 3,802,817 A | 4/1974 | Matsuki |
| 3,848,594 A | 11/1974 | Buell |
| 3,849,241 A | 11/1974 | Butin |
| 3,860,003 A | 1/1975 | Buell |
| 4,340,563 A | 7/1982 | Appel |
| 4,610,678 A | 9/1986 | Weisman |
| 4,662,875 A | 5/1987 | Hirotsu |
| 4,673,402 A | 6/1987 | Weisman |
| 4,699,622 A | 10/1987 | Toussant |
| 4,808,178 A | 2/1989 | Aziz |
| 4,834,735 A | 5/1989 | Alemany |
| 4,846,815 A | 7/1989 | Scripps |
| 4,888,231 A | 12/1989 | Angstadt |
| 4,892,536 A | 1/1990 | DesMarais et al. |
| 4,894,060 A | 1/1990 | Nestegard |
| 4,909,803 A | 3/1990 | Aziz |
| 4,940,464 A | 7/1990 | VanGompel et al. |
| 4,946,527 A | 8/1990 | Battrell |
| 4,963,140 A | 10/1990 | Robertson |
| 4,990,147 A | 2/1991 | Freeland |
| 5,037,416 A | 8/1991 | Allen |
| 5,092,861 A | 3/1992 | Nomura |
| 5,137,537 A | 8/1992 | Herron |
| 5,147,345 A | 9/1992 | Lavon |
| 5,151,092 A | 9/1992 | Buell |
| 5,213,881 A | 5/1993 | Timmons |
| 5,221,274 A | 6/1993 | Buell |
| 5,242,436 A | 9/1993 | Weil |
| 5,246,433 A | 9/1993 | Hasse |
| 5,260,345 A | 11/1993 | Desmarais |
| 5,269,775 A | 12/1993 | Freeland |
| 5,302,675 A | 4/1994 | Sustic |
| 5,342,338 A | 8/1994 | Roe |
| 5,387,207 A | 2/1995 | Dyer |
| 5,397,316 A | 3/1995 | Young |
| 5,499,978 A | 3/1996 | Buell |
| 5,507,736 A | 4/1996 | Clear |
| 5,554,145 A | 9/1996 | Roe |
| 5,569,234 A | 10/1996 | Buell |
| 5,571,096 A | 11/1996 | Dobrin |
| 5,580,411 A | 12/1996 | Nease |
| 5,591,152 A | 1/1997 | Buell |
| 5,607,760 A | 3/1997 | Roe |
| 5,609,587 A | 3/1997 | Roe |
| 5,625,222 A | 4/1997 | Yoneda |
| 5,635,191 A | 6/1997 | Roe |
| 5,643,588 A | 7/1997 | Roe |
| 5,723,546 A | 3/1998 | Sustic |
| 5,865,823 A | 2/1999 | Curro |
| 5,897,545 A | 4/1999 | Kline |
| 5,957,908 A | 9/1999 | Kline |
| 6,004,306 A | 12/1999 | Robles |
| 6,107,537 A | 8/2000 | Elder |
| 6,120,487 A | 9/2000 | Ashton |
| 6,120,489 A | 9/2000 | Johnson |
| 6,432,098 B1 | 8/2002 | Kline |
| 6,992,131 B2 | 1/2006 | Faissat et al. |
| 7,626,073 B2 | 12/2009 | Catalan |
| 8,017,827 B2 | 9/2011 | Hundorf |
| 8,187,240 B2 | 5/2012 | Busam |
| 8,226,625 B2 | 7/2012 | Turner |
| 8,226,626 B2 | 7/2012 | Turner |
| 8,231,595 B2 | 7/2012 | Turner |
| 8,319,005 B2 | 11/2012 | Becker |
| 8,388,594 B2 | 3/2013 | Turner |
| 8,496,637 B2 | 7/2013 | Hundorf |
| 8,865,824 B2 | 10/2014 | Bunnelle |
| 9,060,904 B2 | 6/2015 | Hundorf |
| 9,076,634 B2 | 7/2015 | Brown |
| 9,139,755 B2 | 9/2015 | Bunnelle |
| 9,187,679 B2 | 11/2015 | Bunnelle |
| 9,241,843 B2 | 1/2016 | Bunnelle et al. |
| 9,555,152 B2 | 1/2017 | Bunnelle |
| 9,556,366 B2 | 1/2017 | Bunnelle |
| 9,670,388 B2 | 6/2017 | Bunnelle |
| 9,695,342 B2 | 7/2017 | Sustic |
| 9,937,277 B2 | 4/2018 | Bunnelle |
| 9,943,623 B2 | 4/2018 | Bunnelle |
| 9,994,742 B2 | 6/2018 | Bunnelle |
| 2003/0105183 A1 | 6/2003 | Sharak |
| 2003/0181554 A1 | 9/2003 | Faissat et al. |
| 2004/0081795 A1 | 4/2004 | Wang |
| 2004/0249046 A1 | 12/2004 | Abhari et al. |
| 2007/0083183 A1 | 4/2007 | Bunnelle |
| 2009/0105407 A1 | 4/2009 | Karjala et al. |
| 2011/0054117 A1 | 3/2011 | Hall |
| 2011/0076905 A1 | 3/2011 | Muessig et al. |
| 2011/0104487 A1 | 5/2011 | Schroeyers et al. |
| 2012/0316530 A1 | 12/2012 | Armstrong-Ostle |
| 2013/0060215 A1 | 3/2013 | Knutson |
| 2014/0079919 A1 | 3/2014 | Bunnelle |
| 2014/0147669 A1 | 5/2014 | Thatcher |
| 2014/0257220 A1 | 9/2014 | Neton et al. |
| 2014/0296811 A1 | 10/2014 | Bunnelle |
| 2015/0080511 A1 | 3/2015 | Knutson |
| 2015/0173958 A1 | 6/2015 | Bunnelle |
| 2015/0174286 A1 | 6/2015 | Bunnelle |
| 2016/0289511 A1 | 10/2016 | Sustic et al. |
| 2017/0095587 A1 | 4/2017 | Bunnelle |
| 2017/0095588 A1 | 4/2017 | Bunnelle et al. |
| 2017/0165125 A1 | 6/2017 | Turner |
| 2017/0165130 A1 | 6/2017 | Turner |

(56) References Cited

U.S. PATENT DOCUMENTS

| | | |
|---|---|---|
| 2017/0165133 A1 | 6/2017 | Turner |
| 2017/0165396 A1 | 6/2017 | Turner |
| 2017/0204307 A1 | 7/2017 | Bunnelle |
| 2017/0209616 A1 | 7/2017 | Turner |
| 2018/0002579 A1 | 1/2018 | Hu |
| 2018/0029344 A1 | 2/2018 | Hamm et al. |
| 2018/0078425 A1 | 3/2018 | Bunnelle |
| 2018/0237664 A1 | 8/2018 | Bunnelle |
| 2019/0321241 A1 | 10/2019 | Turner et al. |
| 2019/0321242 A1 | 10/2019 | Turner et al. |
| 2019/0322900 A1 | 10/2019 | Turner et al. |
| 2019/0322901 A1 | 10/2019 | Turner et al. |
| 2019/0322909 A1 | 10/2019 | Turner et al. |

FOREIGN PATENT DOCUMENTS

| | | |
|---|---|---|
| WO | 2013019507 A2 | 2/2013 |
| WO | 2016140944 A1 | 9/2016 |
| WO | 2016208701 A1 | 12/2016 |

OTHER PUBLICATIONS

All Office Actions, U.S. Appl. No. 16/387,689, filed on Apr. 18, 2019.
All Office Actions, U.S. Appl. No. 16/387,704, filed on Apr. 18, 2019.
All Office Actions, U.S. Appl. No. 16/387,712, filed on Apr. 18, 2019.
PCT Search Report and Written Opinion for PCT/US2019/028021 dated Aug. 13, 2019, 17 pages.
RT 2715 Amorphous Polyalphaolefin (APAO), REXtac, year 2022, p. 2.
Benefits to using REXtac APAO, REXtac, year 2022, pp. 1.

ABSORBENT ARTICLE COMPRISING AN ADHESIVE COMPOSITION

CROSS REFERENCE TO RELATED APPLICATION

This application is a continuation of and claims priority under 35 U.S.C. § 120 to U.S. patent application Ser. No. 16/387,712, filed on Apr. 18, 2019, which claims the benefit under 35 USC § 119(e) of U.S. Provisional Patent Application No. 62/660,359 filed on Apr. 20, 2018, each of which are herein incorporated by reference in their entirety.

FIELD

Described herein is an adhesive composition, typically a hot melt adhesive composition, that is used to assemble components into an absorbent article such as a diaper (i.e. the construction adhesive). In particular, described herein are absorbent articles assembled using a construction adhesive that is substantially free of a tackifier.

BACKGROUND

Users, for example caregivers, rely on disposable absorbent articles to make their lives easier. Disposable absorbent articles, such as adult incontinence articles, diapers, and training pants are generally manufactured by combining several components. These components typically include a liquid-permeable topsheet, a liquid-impermeable backsheet attached to the topsheet, and an absorbent core located between the topsheet and the backsheet. When the disposable article is worn, the liquid-permeable topsheet is positioned next to the body of the wearer. The topsheet allows passage of bodily fluids into the absorbent core. The liquid-impermeable backsheet helps prevent leakage of fluids held in the absorbent core. The absorbent core generally is designed to have desirable physical properties, e.g. a high absorbent capacity and high absorption rate, so that bodily fluids can be transported from the skin of the wearer into the disposable absorbent article.

Frequently one or more components of a disposable absorbent article are adhesively bonded together. For example, adhesives have been used to bond individual layers of the absorbent article, such as the topsheet and backsheet together. Adhesives have also been used to bond discrete components, such as fasteners and leg elastics or cuffs, to the article. The adhesive is often called a construction adhesive because it is used to help construct the absorbent article from individual components.

In many instances, an adhesive composition is used as a construction adhesive. Common hot-melt adhesives are made by combining polymer and additive components in a substantially uniform thermoplastic blend. Typical additives may include tackifiers, plasticizers, and/or waxes, for example. While such formulations generally work, they can be costly and their performance properties can be improved. For example, tackifiers, which can comprise up to 65% of an adhesive formula, can be expensive and difficult to source. Therefore, there is a continuing need for improved construction adhesives that offer better performance and lower cost.

SUMMARY

Described herein is an absorbent article having a longitudinal centerline and a lateral centerline, a front waist region with a front waist edge, a rear waist region with a rear waist edge, a crotch region disposed between the front waist region and the rear waist region, and two spaced apart longitudinal side edges joining the front waist edge to the rear waist edge, wherein the absorbent article comprises an assembly of components, and wherein the assembly of components comprises: (a) a topsheet; (b) a backsheet underlying the topsheet; (c) an absorbent core disposed between the topsheet and the backsheet, wherein the absorbent core comprises at least one of a core cover, a dusting layer, an acquisition layer, a distribution layer, and a storage member; (d) at least one additional component selected from the group consisting of: (i) a fastening system for joining the front waist region to the rear waist region when the absorbent article is worn; (ii) barrier cuffs lying adjacent and inboard the two spaced apart longitudinal side edges; (iii) gasketing cuffs lying between each of the two spaced apart longitudinal side edges and the barrier cuffs; (iv) front ears disposed in the front waist region; (v) back ears disposed in the rear waist region; and (vi) a receiving member; and (e) an adhesive composition joining at least two of the assembly of components together, wherein the adhesive composition comprises: (i) from about 70 wt. % to about 90 wt. % of one or more copolymers, wherein the one or more copolymers comprise from about 30 mole % to about 70 mole % of monomer units selected from the group consisting of ethylene, 1-butene, and mixtures thereof; and wherein the one or more copolymers comprise from about 30 mole % to about 70 mole % of propene monomer units; and (ii) from about 10 wt. % to about 30 wt. % of one or more heterophase copolymers; wherein the adhesive composition is free of polyisobutylene; wherein the adhesive composition has a viscosity of from about 2,000 mPa·s to about 11,500 mPa·s at 150° C., as measured by the Viscosity Test Method; wherein the one or more heterophase copolymers comprises a first heterophase copolymer and a second heterophase copolymer; wherein the adhesive composition comprises from about 5 wt. % to about 15 wt. % of the first heterophase copolymer and from about 5 wt. % to about 15 wt. % of the second heterophase copolymer; and wherein the first heterophase copolymer has a higher Enthalpy of Fusion than the second heterophase copolymer, as measured by the Enthalpy of Fusion Test Method.

Also described herein is an absorbent article having a longitudinal centerline and a lateral centerline, a front waist region with a front waist edge, a rear waist region with a rear waist edge, a crotch region disposed between the front waist region and the rear waist region, and two spaced apart longitudinal side edges joining the front waist edge to the rear waist edge, wherein the absorbent article comprises an assembly of components, and wherein the assembly of components comprises: (a) a topsheet; (b) a backsheet underlying the topsheet; (c) an absorbent core disposed between the topsheet and the backsheet, wherein the absorbent core comprises at least one of a core cover, a dusting layer, an acquisition layer, a distribution layer, and a storage member; (d) at least one additional component selected from the group consisting of: (i) a fastening system for joining the front waist region to the rear waist region when the absorbent article is worn; (ii) barrier cuffs lying adjacent and inboard the two spaced apart longitudinal side edges; (iii) gasketing cuffs lying between each of the two spaced apart longitudinal side edges and the barrier cuffs; (iv) front ears disposed in the front waist region; (v) back ears disposed in the rear waist region; and (vi) a receiving member; and (e) an adhesive composition joining at least two of the assembly of components together, wherein the adhesive composition comprises: (i) from about 50 wt. % to about 80 wt. % of one or more copolymers, wherein the one or more copolymers comprise from about 30 mole % to about 70 mole % of monomer units selected from the group consisting of ethylene, 1-butene, and mixtures thereof; and wherein the one or more copolymers comprise from about 30 mole % to about 70 mole % of propene monomer units; and (ii) from about 20 wt. % to about 50 wt. % of one or more heterophase copolymers; wherein the adhesive composition is free of polyisobutylene; wherein the adhesive composition has a viscosity of from about 2,000 mPa·s to about 11,500 mPa·s at 150° C., as measured by the Viscosity Test Method; wherein the adhesive composition has an Enthalpy of Fusion of less than 15 J/g, as measured by the Enthalpy of Fusion Test Method; and wherein the one or more copolymers comprises a first copolymer and a second copolymer, and wherein the adhesive composition comprises from about 40 wt. % to about 75 wt. % of the first copolymer and from about 5 wt. % to about 40 wt. % of the second copolymer.

Also described herein is an absorbent article having a longitudinal centerline and a lateral centerline, a front waist region with a front waist edge, a rear waist region with a rear waist edge, a crotch region disposed between the front waist region and the rear waist region, and two spaced apart longitudinal side edges joining the front waist edge to the rear waist edge, wherein the absorbent article comprises an assembly of components, and wherein the assembly of components comprises: (a) a topsheet; (b) a backsheet underlying the topsheet; (c) an absorbent core disposed between the topsheet and the backsheet, wherein the absorbent core comprises at least one of a core cover, a dusting layer, an acquisition layer, a distribution layer, and a storage member; (d) at least one additional component selected from the group consisting of: (i) a fastening system for joining the front waist region to the rear waist region when the absorbent article is worn; (ii) barrier cuffs lying adjacent and inboard the two spaced apart longitudinal side edges; (iii) gasketing cuffs lying between each of the two spaced apart longitudinal side edges and the barrier cuffs; (iv) front ears disposed in the front waist region; (v) back ears disposed in the rear waist region; and (vi) a receiving member; and (e) an adhesive composition joining at least two of the assembly of components together, wherein the adhesive composition comprises: (i) from about 70 wt. % to about 90 wt. % of one or more copolymers, wherein the one or more copolymers comprise (i) from about 30 mole % to about 70 mole % of 1-butene monomer units; and (ii) from about 30 mole % to about 70 mole % of propene monomer units; and (ii) from about 10 wt. % to about 30 wt. % of one or more heterophase copolymers; wherein the adhesive composition is free of polyisobutylene; wherein the adhesive composition has a viscosity of from about 2,000 mPa·s to about 11,500 mPa·s at 150° C., as measured by the Viscosity Test Method; wherein the adhesive composition has an Enthalpy of Fusion of less than 15 J/g, according to the Enthalpy of Fusion Test Method; and wherein the one or more amorphous copolymers comprises a first copolymer and a second copolymer, and wherein the adhesive composition comprises from about 35 wt. % to about 80 wt. % of the first copolymer and from about 10 wt. % to about 35 wt. % of the second copolymer.

The one or more copolymers comprising (i) from about 30 mole % to about 70 mole % of 1-butene monomer units; and (ii) from about 30 mole % to about 70 mole % of propene monomer units may be in particular an amorphous copolymer(s).

DETAILED DESCRIPTION

As used herein, the following terms shall have the meaning specified thereafter:

"Disposable," in reference to absorbent articles, means that the absorbent articles are generally not intended to be laundered or otherwise restored or reused as absorbent articles (i.e., they are intended to be discarded after a single use and, preferably, to be recycled, composted or otherwise discarded in an environmentally compatible manner).

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, adult incontinence briefs and undergarments, diaper holders and liners, feminine hygiene garments such as panty liners, absorbent inserts, and the like.

"Proximal" and "Distal" refer respectively to the location of an element relatively near to or far from the longitudinal or lateral centerline of a structure (e.g., the proximal edge of a longitudinally extending element is located nearer to the longitudinal centerline than the distal edge of the same element is located relative to the same longitudinal centerline).

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Longitudinal" refers to a direction running substantially perpendicular from a waist edge to an opposing waist edge of the article and generally parallel to the maximum linear dimension of the article. Directions within 45 degrees of the longitudinal direction are considered to be "longitudinal".

"Lateral" refers to a direction running from a longitudinal edge to an opposing longitudinal edge of the article and generally at a right angle to the longitudinal direction. Directions within 45 degrees of the lateral direction are considered to be "lateral."

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Film" refers to a sheet-like material wherein the length and width of the material far exceed the thickness of the material. Typically, films have a thickness of about 0.5 mm or less.

"Water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure (aside from natural forces such as gravity). A layer or a layered structure that is water-impermeable according to this definition may be permeable to water vapor, i.e., may be "vapor-permeable."

"Extendibility" and "extensible" mean that the width or length of the component in a relaxed state can be extended or increased.

"Elastic," "elastomer," and "elastomeric" refer to a material which generally is able to extend to a strain of at least 50% without breaking or rupturing, and is able to recover substantially to its original dimensions after the deforming force has been removed.

"Elastomeric material" is a material exhibiting elastic properties. Elastomeric materials may include elastomeric films, scrims, nonwovens, and other sheet-like structures.

"Outboard" and "inboard" refer respectively to the location of an element disposed relatively far from or near to the longitudinal centerline of the diaper with respect to a second element. For example, if element A is outboard of element B, then element A is farther from the longitudinal centerline than is element B.

"Pant" refers to disposable absorbent articles having a pre-formed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants."

"Nonwoven" fabric or web means a web having a structure of individual fibers or threads that are interlaid, but not in a regular or identifiable manner as in a knitted fabric. Nonwoven fabrics or webs have been formed from many processes such as, for example, meltblowing processes, spunbonding processes, air laying processes, and bonded carded web processes. The basis weight of nonwoven fabrics is usually expressed in ounces of material per square yard (osy) or grams per square meter (gsm) and the fiber diameters are usually expressed in microns. (Note: to convert from osy to gsm, multiply osy by 33.91.)

"Substrate" is used herein to describe a material that is primarily two-dimensional (i.e., in an XY plane) and whose thickness (in a Z direction) is relatively small (i.e. 1/10 or less) in comparison to its length (in an X direction) and width (in a Y direction). Non-limiting examples of substrates include a web, layer or layers of fibrous materials, nonwovens, and films and foils, such as polymeric films or metallic foils, for example. These materials may be used alone or may comprise two or more layers laminated together. As such, a web may be a substrate or may be a laminate of two or more substrates.

"Spunbonded fibers", or "spunbond fibers", means small-diameter fibers that are typically formed by extruding molten thermoplastic material as filaments from a plurality of fine capillaries of a spinneret having a circular or other configuration, with the diameter of the extruded filaments then being rapidly reduced as by, for example, in U.S. Pat. Nos. 4,340,563, 3,692,618, 3,802,817, 3,338,992, 3,341,394, 3,502,763, 3,502,538, and 3,542,615. Spunbond fibers are quenched and generally not tacky when they are deposited onto a collecting surface. Spunbond fibers are generally continuous and often have average diameters larger than about 7 microns, and more particularly between about 10 and 30 microns. A spunbond material, layer, or substrate comprises spunbonded (or spunbond) fibers.

"Meltblown fibers" means fibers formed by extruding a molten material, typically thermoplastic in nature, through a plurality of fine, usually circular, die capillaries as molten threads or filaments into converging high-velocity heated gas (e.g., air) streams that attenuate the filaments of molten material to reduce their diameter, which may be to microfiber diameter. Thereafter, the meltblown fibers are carried by the high-velocity gas stream and are deposited on a collecting surface to form a web of randomly dispersed meltblown fibers. Such a process is disclosed for example, in U.S. Pat. No. 3,849,241. Meltblown fibers are microfibers which may be continuous or discontinuous, are generally smaller than 10 microns in diameter, and are generally self-bonding when deposited onto a collecting surface "Microfibers" means small-diameter fibers having an average diameter not greater than about 100 microns, for example, having a diameter of from about 0.5 microns to about 50 microns, more specifically microfibers may also have an average diameter of from about 1 micron to about 20 microns. Microfibers having an average diameter of about 3 microns or less are commonly referred to as ultra-fine microfibers. A description of an exemplary process of making ultra-fine microfibers may be found in, for example, U.S. Pat. No. 5,213,881.

"Homopolymer" means a polymer resulting from the polymerization of a single monomer, i.e., a polymer consisting essentially of a single type of repeating unit.

"Copolymer(s)" refers herein to polymer(s) formed by the polymerization of at least two different monomers. The term "copolymer" can include terpolymers, which contain three types of different monomers.

"Devoid of," "free of," and the like, as those terms are used herein, means that the adhesive composition does not have more than trace amounts of background levels of a given material, ingredient, or characteristic following these qualifiers; the amount of the material or ingredient does not cause harm or irritation that consumers typically associate with the material or ingredient; or the material or ingredient was not added to the adhesive composition intentionally. In some applications, "devoid of" and "free of" can mean there is no measurable amount of the material or ingredient. For example, the adhesive composition in some forms can contain no measurable amount of a tackifier.

"Heterophase" polymer refers herein to a polymer having an amorphous character and at least some substantial crystalline content that can provide cohesive strength in the cooled adhesive mass (in particular the polymer having an enthalpy of fusion of at least 20.0 J/g, as measured with the Enthalpy of Fusion Test Method described herein). The crystalline content can be in the form of stereoregular blocks or sequences.

"Amorphous" refers herein to the substantial absence of crystallinity, in particular to polymers having an enthalpy of fusion of less than 20.0 J/g, as measured with the Enthalpy of Fusion Test Method described herein.

"Sequence or block" means a polymer portion of repeating monomer that is similar in composition, crystallinity or other aspect.

"Open time" means the amount of time elapsed between application of a molten hot melt adhesive composition to a first substrate, and the time when useful tackiness or wetting out of the adhesive on a substrate effectively ceases due to solidification of the adhesive composition. Open time is also referred to as "working time."

"Substantially" means generally the same or uniform but allowing for or having minor fluctuations from a defined property, definition, etc. For example, small measureable or immeasurable fluctuations in a measured property described herein, such as viscosity, melting point, etc. may result from human error or methodology precision. Other fluctuations are caused by inherent variations in the manufacturing process, thermal history of a formulation, and the like. The adhesive compositions of the, nonetheless, would be said to be substantially having the property as reported.

"Major proportion" means that a material or monomer is used at greater than 50 wt. %.

"Primary component" means that a material or monomer is the more common substance or has the higher concentration in the mixture or polymer compared to others but may not be as much as 50 wt. %.

"Hot-melt processable" means that an adhesive composition may be liquefied using a hot-melt tank (i.e., a system in which the composition is heated so that it is substantially in liquid form) and transported via a pump (e.g., a gear pump or positive-displacement pump) from the tank to the point of application proximate a substrate or other material; or to another tank, system, or unit operation (e.g., a separate system, which may include an additional pump or pumps, for delivering the adhesive to the point of application). Hot-melt tanks used to substantially liquefy a hot-melt adhesive typically operate in a range from about 38° C. to about 230° C. Generally, at the point of application, the substantially liquefied adhesive composition will pass through a nozzle or bank of nozzles, but may pass through some other mechanical element such as a slot. A hot-melt processable adhesive composition is to be contrasted with a composition that requires a conventional extruder, and the attendant pressures and temperatures characteristic of an extruder, to liquefy, mix, and/or convey the composition. While a hot-melt tank and pump in a hot-melt processing system can handle adhesive-composition viscosities in a range from about 1000 centipoise to about 10,000 centipoise, an extruder can handle and process adhesive-composition viscosities in a range from about 10,000 centipoise to viscosities of several hundred thousand centipoise.

Unless otherwise noted, "Laminated structure" or "laminate" means a structure in which one layer, material, component, web, or substrate is adhesively bonded, at least in part, to another layer, material, component, web, or substrate. As stated elsewhere in this application, a layer, material, component, web, or substrate may be folded over and adhesively bonded to itself to form a "laminated structure" or "laminate."

Figure 1:
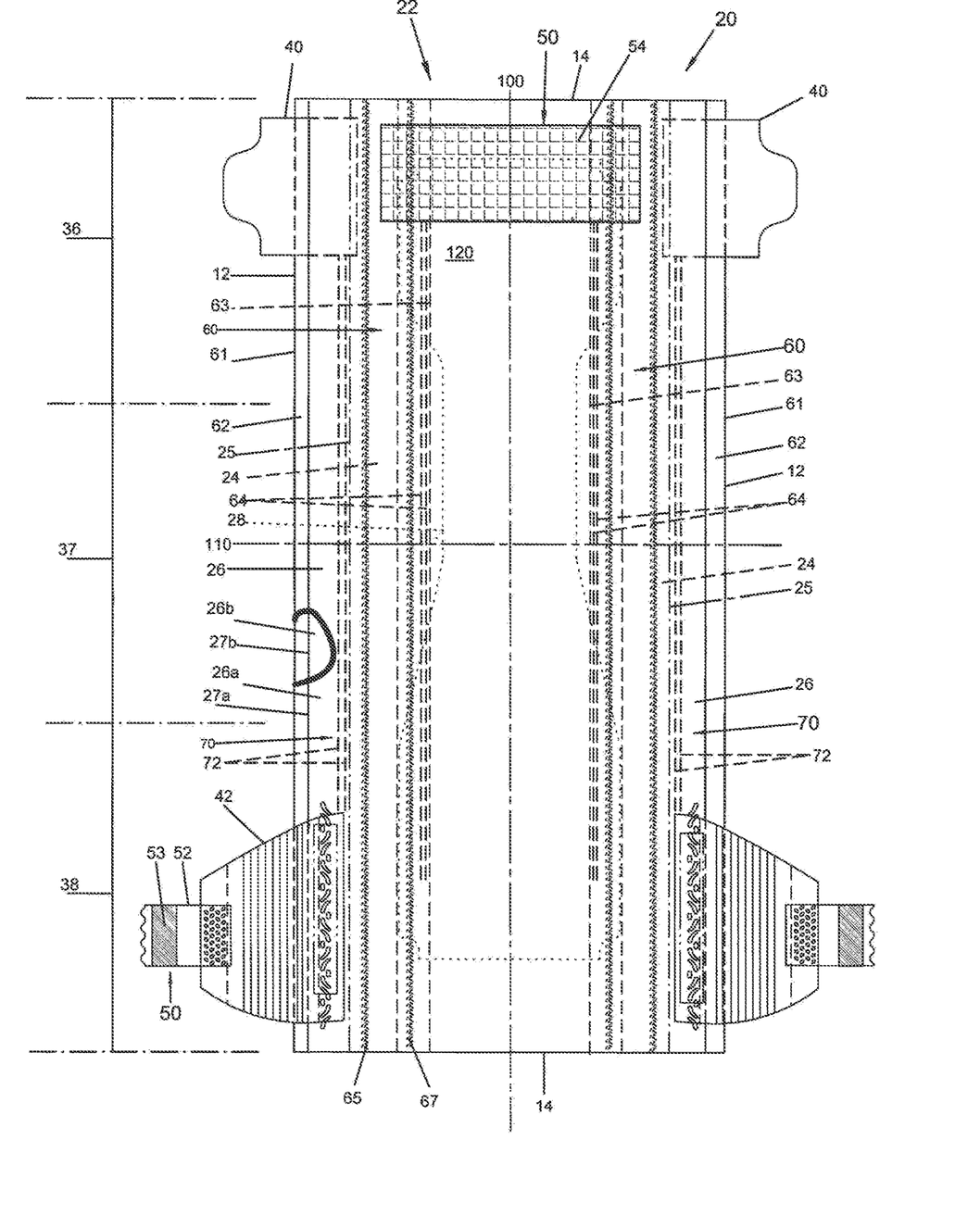
FIG. 1 is a plan view of an exemplary absorbent article in a flat, uncontracted state.

FIG. 1 is a plan view of an exemplary, non-limiting embodiment of a diaper 20 of the present invention in a flat, uncontracted state (i.e., without elastic induced contraction). The garment-facing surface 120 of the diaper 20 is facing the viewer. The diaper 20 includes a longitudinal centerline 100 and a lateral centerline 110. The diaper 20 may comprise a chassis 22. The diaper 20 and chassis 22 are shown to have a front waist region 36, a rear waist region 38 opposed to the front waist region 36, and a crotch region 37 located between the front waist region 36 and the rear waist region 38. The waist regions 36 and 38 generally comprise those portions of the diaper 20 which, when worn, encircle the waist of the wearer. The waist regions 36 and 38 may include elastic elements such that they gather about the waist of the wearer to provide improved fit and containment. The crotch region 37 is that portion of the diaper 20 which, when the diaper 20 is worn, is generally positioned between the legs of the wearer.

The outer periphery of chassis 22 is defined by longitudinal side edges 12 and end edges 14. The chassis 22 may have opposing longitudinal side edges 12 that are oriented generally parallel to the longitudinal centerline 100. However, for better fit, longitudinal side edges 12 may be curved or angled to produce, for example, an "hourglass" shape diaper when viewed in a plan view. The chassis 22 may have opposing lend edges 14 that are oriented generally parallel to the lateral centerline 110.

The chassis 22 may comprises a liquid permeable topsheet 24 having longitudinal side edges 25, a backsheet 26, and an absorbent core 28 between the topsheet 24 and the backsheet 26. The absorbent core 28 may have a body-facing surface and a garment facing-surface. The topsheet 24 may be joined to the core 28 and/or the backsheet 26. The backsheet 26 may be joined to the core 28 and/or the topsheet 24. It should be recognized that other structures, elements, or substrates may be positioned between the core 28 and the topsheet 24 and/or backsheet 26. In certain embodiments, the chassis 22 comprises the main structure of the diaper 20 with other features may added to form the composite diaper structure. While the topsheet 24, the backsheet 26, and the absorbent core 28 may be assembled in a variety of well-known configurations, preferred diaper configurations are described generally in U.S. Pat. Nos. 3,860,003; 5,151,092; 5,221,274; 5,554,145; 5,569,234; 5,580,411; and 6,004,306.

The topsheet 24 is generally a portion of the diaper 20 that may be positioned at least in partial contact or close proximity to a wearer. Suitable topsheets 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 24 is generally supple, soft feeling, and non-irritating to a wearer's skin. Generally, at least a portion of the topsheet 24 is liquid pervious, permitting liquid to readily penetrate through the thickness of the topsheet 24. A particularly preferred topsheet 24 is available from BBA Fiberweb, Brentwood, TN as supplier code 055SLPV09U.

Any portion of the topsheet 24 may be coated with a lotion as is known in the art. Examples of suitable lotions include those described in U.S. Pat. Nos. 5,607,760; 5,609,587; 5,635,191; and 5,643,588. The topsheet 24 may be fully or partially elasticized or may be foreshortened so as to provide a void space between the topsheet 24 and the core 28. Exemplary structures including elasticized or foreshortened topsheets are described in more detail in U.S. Pat. Nos. 4,892,536; 4,990,147; 5,037,416; and 5,269,775.

The absorbent core 28 may comprise a wide variety of liquid-absorbent materials commonly used in disposable diapers and other absorbent articles. Examples of suitable absorbent materials include comminuted wood pulp, which is generally referred to as air felt creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. These materials may be combined to provide a core 28 in the form of one or more layers (individual layers not shown) that may include fluid handling layers such as acquisition layers, distribution layers and storage layers. The absorbent core 28 may comprise a substrate layer, absorbent polymer material, and a fibrous layer of adhesive (not shown). Such absorbent cores 28 may also include layers (not shown) to stabilize other core components. Such layers include a core cover and a dusting layer. A suitable material for such layers is a spunbonded/meltblown/spunbonded nonwoven having a basis weight between about 10 and 15 g/m$^2$ (the meltblown layer comprises <5 g/m$^2$) as is available from Avgol America, Inc. of Knoxville, NC. For example, Exemplary absorbent structures for use as the absorbent core 28 are described in U.S. Pat. Nos. 4,610,678; 4,673,402; 4,834,735; 4,888,231; 5,137,537; 5,147,345; 5,342,338; 5,260,345; 5,387,207; 5,397,316; 5,625,222. To reduce the overall size and/or thickness of the absorbent core, and thereby improve wearer comfort and reduce the volume of disposable waste created by a soiled insert, it may be desired to construct an absorbent core using the lowest volumes of core materials possible within performance constraints. Toward this end, examples of suitable materials and constructions for a suitable absorbent core are described in, but are not limited to, U.S. application Ser. Nos. 12/141,122 and 12/141,124; and U.S. Pat. Nos. 8,017,827; and 8,496,637. These generally describe absorbent core constructions that minimize or eliminate the need for and inclusion of airfelt or other forms of cellulose fiber in combination with particles of superabsorbent polymer (hereinafter, "substantially airfelt-free cores"). The adhesives of the present invention may be used within or near the core to immobilize the core, immobilize absorbent material, or to bond the core substrate to the absorbent polymer material, among other uses. The construction of the absorbent core and adhesives used within the core may be such as described in U.S. Pat. Nos. 8,319,005 and 8,187,240, and in U.S. Publication No. 2012/0316530. In some embodiments, the adhesive may be fibrous or be a net-like structure.

The backsheet 26 is generally positioned such that it may be at least a portion of the garment-facing surface 120 of the diaper 20. Backsheet 26 may be designed to prevent the exudates absorbed by and contained within the diaper 20 from soiling articles that may contact the diaper 20, such as bed sheets and undergarments. In certain embodiments, the backsheet 26 is substantially water-impermeable. Suitable backsheet 26 materials include films such as those manufactured by Tredegar Industries Inc. of Terre Haute, IN and sold under the trade names X15306, X10962, and X10964. Other suitable backsheet 26 materials may include breathable materials that permit vapors to escape from the diaper 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, TX, under the designation EXXAIRE. Suitable breathable composite materials comprising polymer blends are available from Clopay Corporation, Cincinnati, OH under the name HYTREL blend P18-3097. Such breathable composite materials are described in greater detail in PCT Application No. WO 95/16746 and U.S. Pat. No. 5,865,823. Other breathable backsheets including nonwoven webs and apertured formed films are described in U.S. Pat. No. 5,571,096. An exemplary, suitable backsheet is disclosed in U.S. Pat. No. 6,107,537. Other suitable materials and/or manufacturing techniques may be used to provide a suitable backsheet 26 including, but not limited to, surface treatments, particular film selections and processing, particular filament selections and processing, etc.

Backsheet 26 may also consist of more than one layer, as illustrated in the cut-away of FIG. 1. The backsheet 26 may comprise an outer cover 26a and an inner layer 26b. The outer cover 26a may have longitudinal side edges 27a and the inner layer 26b may have longitudinal side edges 27b. The outer cover 26a may be made of a soft, non-woven material. The inner layer 26b may be made of a substantially water-impermeable film. The outer cover 26a and an inner layer 26b may be joined together by adhesive or any other suitable material or method. A particularly suitable outer cover 26a is available from Corovin GmbH, Peine, Germany as supplier code A18AH0, and a particularly suitable inner layer 26b is available from RKW Gronau GmbH, Gronau, Germany as supplier code PGBR4WPR. While a variety of backsheet configurations are contemplated herein, it would be obvious to those skilled in the art that various other changes and modifications can be made without departing from the spirit and scope of the invention.

The diaper 20 may also include a fastening system 50. When fastened, the fastening system 50 interconnects the front waist region 36 and the rear waist region 38 resulting in a waist circumference that may encircle the wearer during wear of the diaper 20. The fastening system 50 may comprises a fastener such as tape tabs, hook and loop fastening components, interlocking fasteners such as tabs & slots, buckles, buttons, snaps, and/or hermaphroditic fastening components, although any other known fastening means are generally acceptable. Some exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098. The fastening system 50 may also provide a means for holding the article in a disposal configuration as disclosed in U.S. Pat. No. 4,963,140. The fastening system 50 may also include primary and secondary fastening systems, as disclosed in U.S. Pat. No. 4,699,622. The fastening system 50 may be constructed to reduce shifting of overlapped portions or to improve fit as disclosed in U.S. Pat. Nos. 5,242,436; 5,499,978; 5,507,736; and 5,591,152.

FIG. 1 depicts a fastening system 50 having an engaging member 52 and a receiving member 54. The engaging member 52 is shown having an engaging surface 53 that may comprise hooks, loops, an adhesive, a cohesive, or other fastening member. The receiving member 54 may have a surface that allows for engagement of the engaging member 52. The receiving member 54 may comprise hooks, loops, an adhesive, a cohesive, or other fastening component that can receive the engaging member 52. Suitable engaging member 52 and receiving member 54 combinations include but are not limited to hooks/loop, hooks/hooks, adhesive/polymeric film; cohesive/cohesive, adhesive/adhesive; tab/slot; and button/button hole.

The diaper 20 may include barrier cuffs 60 and/or gasketing cuffs 70. Gasketing cuffs 70 may also be referred to as outer leg cuffs, leg bands, side flaps, leg cuffs, or elastic cuffs. Barrier cuffs 60 may also be referred to as second cuffs, inner leg cuffs or "stand-up" elasticized flaps.

The gasketing cuff 70 may be substantially inelastic or may be elastically extensible to dynamically fit at the wearer's leg. The gasketing cuff 70 may be formed by one or more elastic members 72 (such as elastic strands) operatively joined to the topsheet 24, backsheet 26, or any other suitable substrate used in the formation of the diaper 20. Suitable gasketing cuff construction is further described in U.S. Pat. No. 3,860,003

The barrier cuff 60 may have a distal edge 61 and a proximal edge 63 that run substantially parallel to the longitudinal centerline 100. The barrier cuff 60 may span the entire longitudinal length of the diaper 20. The barrier cuff 60 may be formed by a flap 62 and an elastic member 64 (such as elastic strands). The flap 62 may be a continuous extension of any of the existing materials or elements that form the diaper 20. In other embodiments, such as shown in FIG. 1, the barrier cuff 60 may be a discrete element. In such embodiments, the barrier cuff 60 comprising the flap 62 and the elastic member 64 may be formed then joined to the chassis 22 by a bond 65.

The flap 62 may comprise a variety of substrates such as plastic films and woven or nonwoven webs of natural fibers (e.g., wood or cotton fibers), synthetic fibers (e.g., polyester or polypropylene fibers), or a combination of natural and synthetic fibers. In certain embodiments, the flap 62 may comprise a nonwoven web such as spunbond webs, meltblown webs, carded webs, and combinations thereof (e.g., spunbond-meltblown composites and variants). Laminates of the aforementioned substrates may also be used to form the flap 62. A particularly suitable flap may comprise a nonwoven available from BBA Fiberweb, Brentwood, TN as supplier code 30926. A particularly suitable elastic member is available from Invista, Wichita, KS as supplier code T262P. Further description of diapers having barrier cuffs and suitable construction of such barrier cuffs may be found in U.S. Pat. Nos. 4,808,178 and 4,909,803. The elastic member 64 generally spans the longitudinal length of the barrier cuff 60. In other embodiments, the elastic member 64 may span at least the longitudinal length of the barrier cuff 60 within the crotch region 37. It is desirable that the elastic member 64 exhibits sufficient elasticity such that the proximal edge 63 of the barrier cuff 60 remains in contact with the wearer during normal wear, thereby enhancing the barrier properties of the barrier cuff 60. The elastic member 64 may be connected to the flap 62 at opposing longitudinal ends. In certain embodiments, the flap 62 may be folded over onto itself so as to encircle the elastic member 64. A bond 67 may be used to secure the folded section of the flap 62.

The barrier cuffs 60 and/or gasketing cuffs 70 may be treated, in full or in part, with a lotion, as described above with regard to topsheets, or may be fully or partially coated with a hydrophobic surface coating as detailed in U.S. application Ser. No. 11/055,743, which was filed Feb. 10, 2005.

The diaper 20 may include front ears 40 and back ears 42. The front and/or back ears 40, 42 may be unitary elements of the diaper 20 (i.e., they are not separately manipulative elements secured to the diaper 20, but rather are formed from and are extensions of one or more of the various layers of the diaper). In certain embodiments, the front and/or back ears 40, 42 may be discrete elements that are joined to the chassis 22, as shown in FIG. 1. Discrete front and/or back ears 40, 42 may be joined to the chassis 22 by any bonding method known in the art such as adhesive bonding, pressure bonding, heat bonding, and the like. In other embodiments, the front and/or back ears 40, 42 may comprise a discrete element joined to the chassis 22 with the chassis 22 having a layer, element, or substrate that extends over the front and/or back ear 40, 42. The front ears 40 and back ears 42 may be extensible, inextensible, elastic, or inelastic. The front ears 40 and back ears 42 may be formed from nonwoven webs, woven webs, knitted fabrics, polymeric and elastomeric films, apertured films, sponges, foams, scrims, and combinations and laminates thereof. In certain embodiments the front ears 40 and back ears 42 may be formed of a nonwoven/elastomeric material laminate or a nonwoven/elastomeric material/nonwoven laminate. A suitable elastic back ear 42 may be a laminate comprising an elastomeric film (such as is available from Tredegar Corp, Richmond, VA, as supplier code X25007) disposed between two nonwoven layers (such as is available from BBA Fiberweb, Brentwood, TN as supplier code FPN332). While the following embodiments are directed to back ear 42 design and construction, these embodiments are equally applicable to front ear 40 design and construction. It should be recognized that any combination of the following embodiments may be used for the back ear 42 and/or the front ear 40.

In alternative embodiments, the diaper 20 may be preformed by the manufacturer to create a pant. A pant may be preformed by any suitable technique including, but not limited to, joining together portions of the article using refastenable and/or non-refastenable bonds (e.g., seam, weld, adhesive, cohesive bond, fastener, etc.). For example, the diaper 20 of FIG. 1 may be manufactured with the fastening system 50 engaged (i.e., the engaging member 52 is joined to the receiving member 54). As an additional example, the diaper 20 of FIG. 1 may be manufactured with the front ears 40 joined to the back ears 42 by way of a bond such as an adhesive bond, a mechanical bond, or some other bonding technique known in the art. Suitable pants are disclosed in U.S. Pat. Nos. 5,246,433; 5,569,234; 6,120,487; 6,120,489; 4,940,464; 5,092,861; 5,897,545; and 5,957,908.

As noted above, a construction adhesive is typically used to join components of an absorbent article as the absorbent article is being assembled. Nonlimiting examples of such joinder using the construction adhesive include but are not limited to:

core cover to dusting layer sealing;
backsheet 26 to core 28;
elastic member 64 to nonwoven and/or film to form a barrier cuff 60 or a gasketing cuff 70.
nonwoven to vapor permeable film to form a backsheet 26;
barrier cuffs to topsheet 24;
receiving member 54 to topsheet 24;
ear 40, 42 to backsheet 26.
core substrate layer to core absorbent polymer material As will be recognized, many of these uses involve joinder of a nonwoven material to another material. In some instances nonwoven material is joined to another nonwoven. In other instances, a nonwoven may be joined to a film.

Nonwovens in the present invention may be such as those disclosed in U.S. Patent Application Nos. 61/837,286, 8,388,594, 8,226,625, 8,231,595, and 8,226,626.

Adhesive Composition

Described herein is an adhesive composition comprising from about 70 wt. % to about 90 wt. % of one or more copolymers, alternatively from about 75 wt. % to about 85 wt. %, alternatively from about 50 wt. % to about 80 wt. %, alternatively from about 55 wt. % to about 75 wt. %, alternatively from about 60 wt. % to about 70 wt. %, alternatively from about 30 wt. % to about 55 wt. %, alternatively from about 35 wt. % to about 45 wt. %, and alternatively from about 40 wt. % to about 50 wt. % of one or more copolymers. The one or more copolymers may be an amorphous copolymer.

The one or more copolymers can comprise from about 30 wt. % to about 70 wt. %, alternatively from about 35 wt. % to about 65 wt. %, alternatively from about 40 wt. % to about 60 wt. %, alternatively from about 40 wt. % to about 55 wt. %, alternatively from about 45 wt. % to about 55 wt. %, alternatively from about 44 wt. % to about 46 wt. %, and alternatively from about 48 wt. % to about 52 wt. % of propene monomer units. The percentage of propene monomer units may be determined by a suitable method, such as nuclear magnetic resonance or infrared spectroscopies, known to those of skill in the art.

The one or more copolymers can comprise from about 30 wt. % to about 70 wt. %, alternatively from about 35 wt. % to about 65 wt. %, alternatively from about 40 wt. % to about 60 wt. %, alternatively from about 45 wt. % to about 60 wt. %, alternatively from about 45 wt. % to about 55 wt. %, alternatively from about 50 wt. % to about 60 wt. %, alternatively from about 54 wt. % to about 56 wt. %, and alternatively from about 48 wt. % to about 52 wt. % of 1-butene monomer units. The percentage of 1-butene monomer units may be determined by a suitable method, such as nuclear magnetic resonance or infrared spectroscopies, known to those of skill in the art.

The one or more copolymers can comprise from about 1 wt. % to about 40 wt. %, alternatively from about 2 wt. % to about 30 wt. %, alternatively from about 5 wt. % to about 20 wt. %, and alternatively from about 5 wt. % to about 15 wt. % of one or more comonomer units selected from the group consisting of ethylene, 4-methyl-1-pentene, pentene-1,2-methylpentene-1,3methylbutene-1, heptene-1, dimethylpentene-1, trimethylbutene-1, ethylpentene-1, methylpentene-1, trimethylpentene-1, methylethylpentene-1, diethylbutene-1, propylpentane-1, decene-1, methylnonene-1, nonene-1, trimethylheptene-1, methylethylbutene-1, dodecene-1, and hexadodecene-1, and combinations thereof.

The one or more copolymers can comprise a first copolymer and a second copolymer. The adhesive composition can comprise from about 35 wt. % to about 80 wt. %, alternatively from about 45 wt. % to about 70 wt. %, alternatively from about 40 wt. % to about 75 wt. %, alternatively from about 55 wt. % to about 65 wt. %, alternatively from about 40 wt. % to about 55 wt. %, and alternatively from about 50 wt. % to about 60 wt. % of the first copolymer. The adhesive composition can comprise from about 5 wt. % to about 40 wt. %, alternatively from about 10 wt. % to about 35 wt. %, alternatively from about 15 wt. % to about 30 wt. %, alternatively from about 20 wt. % to about 25 wt. %, and alternatively from about 10 wt. % to about 45 wt. % of the second copolymer.

The one or more copolymers can be prepared by the methods described in U.S. Pat. Nos. 5,302,675 and 5,723,546, which are both expressly incorporated herein. The copolymer may be prepared using a single-site catalyst system, multiple single-site catalyst systems, or Ziegler Natta catalyst system. Monomers used to prepare the copolymer can be obtained from one or more carbon-based sources, e.g., biomass from animal and/or vegetable fats. The monomers can also be obtained from renewable feed stocks provided by, e.g., Neste's Rotterdam Refinery (Neste, Finland). Adhesive compositions comprising the copolymer can be prepared by combining the copolymer and at least one optional ingredient (e.g., an optical brightener, other copolymers), if desired. The copolymer can be prepared into a final adhesive composition product by heating the primary copolymer to elevated temperatures (e.g., about 135 to about 175° C.) that melts the copolymer. Once molten, one or more optional ingredients (e.g., additive or other polymers components) can be added to the primary copolymer. A mixer can be used to mix the components together into a final adhesive composition.

The one or more copolymers can be selected from REX-tac$^R$ copolymers 2815, 2715, 2788, 2730, and 2830. See, for example, Sustic, U.S. Pat. No. 5,723,546, which is expressly incorporated by reference, for a description of additional exemplary copolymers.

The adhesive composition can comprise from about 10 wt. % to about 30 wt. %, alternatively from about 15 wt. % to about 25 wt. %, alternatively from about 20 wt. % to about 60 wt. %, alternatively from about 20 wt. % to about 50 wt. %, alternatively from about 25 wt. % to about 55 wt. %, alternatively from about 30 wt. % to about 40 wt. %, and alternatively from about 25 wt. % to about 35 wt. % of one or more heterophase copolymers.

The one or more heterophase copolymers can comprise a first heterophase copolymer and a second heterophase copolymer. The adhesive composition can comprise from about 2 wt. % to about 18 wt. %, alternatively from about 5 wt. % to about 15 wt. %, alternatively from about 10 wt. % to about 25 wt. %, alternatively from about 15 wt. % to about 20 wt. %, and alternatively from about 8 wt. % to about 12 wt. % of the first heterophase copolymer. The adhesive composition can comprise from about 2 wt. % to about 18 wt. %, alternatively from about 5 wt. % to about 15 wt. %, alternatively from about 10 wt. % to about 25 wt. %, alternatively from about 15 wt. % to about 20 wt. %, and alternatively from about 8 wt. % to about 12 wt. % of the second heterophase copolymer. The first heterophase copolymer can have a higher or lower Enthalpy of Fusion than the second heterophase copolymer, as measured by the Enthalpy of Fusion Test Method described herein.

The one or more heterophase copolymers may be made using one or more metallocene catalyst blends that obtain a desired heterophase structure.

The one or more heterophase copolymers can include propene monomer units and/or one or more $C_2$ or $C_{4-20}$ α-olefin monomer units. The one or more heterophase copolymers can comprise from about 99.5 wt. % to about 70 wt. %, or about 95 to about 75 wt. % of propene monomer units.

In addition to propene monomer units, the one or more heterophase copolymers can comprise from about 0.1 wt. % to 30 wt. %, or from about 5 wt. % to 25 wt. % of $C_{2,4}$ or $C_{5-10}$ alpha-olefin monomer units.

The one or more heterophase copolymers can comprise amorphous blocks and crystalline blocks for providing good cohesive strength in the adhesive composition.

Possible examples of the one or more heterophase copolymers can include polyolefins such as polyethylene, polypropylene, and copolymers thereof, such as metallocene-technology based propylene-ethylene copolymers sold by Clariant under the trade name Licocene™, such as Licocene PP-1302 and Licocene PP-2502. Other suitable heterophase copolymers can include polypropylene-based elastomers and polyolefin elastomers described in U.S. Pat. No. 8,865,824, which is incorporated herein by its entirety. The one or more heterophase copolymers can also include heterophasic polypropylene homopolymers (e.g., L-MODU), supplied by Idemitsu Kosan.

Known methods of polymerization and synthesis processes can used to prepare the one or more heterophase copolymers. For example, metallocene catalysts or Zeigler-Natta catalysts may be used for polymerization of an olefin monomer or monomer mixture of the one or more heterophase copolymers, as described in U.S. Pat. No. 8,865,824, which is incorporated herein by its entirety.

The adhesive composition can comprise less than 20 wt. %, alternatively less than 10 wt. %, alternatively less than 5 wt. %, alternatively less than 3 wt. %, alternatively less than 2 wt. %, and alternatively less than 1 wt. %, alternatively less than 0.5 wt. %, and alternatively less than 0.1 wt. % of a tackifier. Exemplary tackifiers can include aliphatic hydrocarbon resins, aromatic modified aliphatic hydrocarbon resins, hydrogenated poly-cyclopentadiene resins, poly-cyclopentadiene resins, gum rosins, gum rosin esters, wood rosins, wood rosin esters, tall oil rosins, tall oil rosin esters, poly-terpenes, aromatic modified poly-terpenes, terpene-phenolics, aromatic modified hydrogenated poly-cyclopentadiene resins, hydrogenated aliphatic resins, hydrogenated aliphatic aromatic resins, hydrogenated terpenes and modified terpenes, and hydrogenated rosin esters.

The adhesive composition can be free of a tackifier. There are significant advantages to minimizing or avoiding the use of a tackifier as it may reduce the cost of the adhesive composition, as well as eliminate an additional ingredient and potential issues that may be associated with supplying the additional ingredient. Furthermore, tackifiers can impart undesirable odor in disposable articles and can also act as carriers of low molecular weight plasticizers (e.g., process oils that are used in SBC based adhesives) that can weaken the polyethylene back sheet materials used in absorbent articles and textile articles.

The adhesive composition can be free of polyisobutylene. The adhesive composition can comprise less than 10 wt. %, alternatively less than 5 wt. %, alternatively less than 3 wt. %, alternatively less than 2 wt. %, and alternatively less than 1 wt. %, alternatively less than 0.5 wt. %, and alternatively less than 0.1 wt. % of polyisobutylene.

Adhesive Composition Properties

The copolymer, as well as adhesive compositions comprising the copolymer, can have a viscosity of from about 2,000 mPa·s to about 11,500 mPa·s, alternatively from about 3,000 mPa·s to about 8,500 mPa·s, alternatively from about 4,000 mPa·s to about 6,500 mPa·s, alternatively from about 4,500 mPa·s to about 6,000 mPa·s, alternatively from about 5,000 mPa·s to about 5,500 mPa·s, alternatively less than 7,500 mPa·s, and alternatively less than 6,500 mPa·s at 150° C., as measured by the Viscosity Test Method described herein.

The copolymer, as well as adhesive compositions comprising the copolymer, can have a rheology and thermal stability suitable for use with conventional hot melt adhesive application equipment. The copolymer, as well as adhesive compositions comprising the copolymer, having a desired viscosity at the application temperature, can facilitate flow of the copolymer, as well as adhesive compositions comprising the copolymer, through a coating apparatus, e.g., a coating die or a spray nozzle.

Desirable viscosity values can be useful for ensuring that the copolymer, as well as adhesive compositions comprising the copolymer, is compatible with adhesive application methods and equipment. For example, a viscosity value that is too high may not be compatible with certain application methods and equipment, e.g., spraying methods and nozzles.

The copolymer, as well as adhesive compositions comprising the copolymer, can have an Enthalpy of Fusion at 1° C./min cooling rate of less than 17 J/g, alternatively less than 16.5 J/g, alternatively less than 16 J/g, alternatively from about 6.5 J/g to 17 J/g, alternatively from about 7 J/g to about 16.5 J/g, alternatively from about 8 J/g to about 16 J/g, alternatively from about 8.7 J/g to about 15.8 J/g, and alternatively from about 10 J/g to about 16 J/g, as measured by the Enthalpy of Fusion Test Method described herein.

The copolymer, as well as adhesive compositions comprising the copolymer, can have a Tensile Strength at Yield of from about 0.5 MPa to about 1.5 MPa, alternatively from about 0.7 MPa to about 1.4 MPa, alternatively from about 0.8 MPa to about 1.35 MPa, alternatively from about 0.9 MPa to about 1.3 MPa, and alternatively from about 0.95 MPa to about 1.25 MPa, as measured by the Tensile Strength Test Method described herein. In some applications, a Tensile Strength at Yield value that is too low may indicate that the copolymer, as well as adhesive compositions comprising the copolymer, is too week and will not provide sufficient tensile strength for a product during use. Alternatively, in some applications, a Tensile Strength at Yield value that is too high may indicate that the copolymer, as well as adhesive compositions comprising the copolymer, is too stiff and cannot sufficiently absorb the stresses applied to the copolymer, as well as adhesive compositions comprising the copolymer, during product use.

The copolymer, as well as adhesive compositions comprising the copolymer, can exhibit surprisingly high values in the Static Peel Time Test Method described herein, as shown in Table 2 below. The copolymer, as well as adhesive compositions comprising the copolymer, can have a Static Peel Time of at least 220 seconds, alternatively at least 230 seconds, alternatively from about 220 seconds to about 750 seconds, alternatively from about 225 seconds to about 600 seconds, alternatively from about 230 seconds to about 500 seconds, and alternatively from about 230 seconds to about 400 seconds, and alternatively from about 235 seconds to about 350 seconds, when performed using a 25-gram weight and a 40-mm wide test sample having a coat weight of about 2.2 gsm, as measured by the Static Peel Time Test Method described herein.

The copolymer, as well as adhesive compositions comprising the copolymer, can have a Needle Penetration of from about 10 decimillimeters to about 35 decimillimeters, alternatively from about 15 decimillimeters to about 30 decimillimeters, and alternatively from about 17 decimillimeters to about 21 decimillimeters, as measured by the Needle Penetration Test Method described herein. In some applications, a Needle Penetration value that is too high may indicate that the copolymer, as well as adhesive compositions comprising the copolymer, is too soft and will not provide sufficient bond strength for a product, leading to a cohesive failure of the adhesive composition in the bond. Alternatively, in some applications, a Needle Penetration that is too low may indicate that the copolymer, as well as adhesive compositions comprising the copolymer, is too stiff and cannot sufficiently absorb the stresses applied to the copolymer, as well as adhesive compositions comprising the copolymer, during product use.

The copolymer, as well as adhesive compositions comprising the copolymer, can have a density of from about 0.4 $g/cm^3$ to about 0.87 $g/cm^3$, alternatively from about 0.5 $g/cm^3$ to about 0.85 $g/cm^3$, alternatively from about 0.7 $g/cm^3$ to about 0.85 $g/cm^3$, alternatively from about 0.75 $g/cm^3$ to about 0.85 $g/cm^3$, and alternatively from about 0.8 $g/cm^3$ to about 0.85 $g/cm^3$ at 150° C.

The copolymer, as well as adhesive compositions comprising the copolymer, can have a Storage Modulus at 37° C. of from about 3 MPa to about 9.5 MPa, alternatively from about 4.5 MPa to about 9.5 MPa, alternatively from about 5 MPa to about 9.25 MPa, and alternatively from about 5.5 MPa to about 9.1 MPa, as measured by the Oscillatory Rheometry Test described herein.

The copolymer, as well as adhesive compositions comprising the copolymer, can have a Yield Stress at 37° C. of from about 0.8 MPa to about 1.45 MPa, alternatively from about 0.9 MPa to about 1.4 MPa, alternatively from about 1 to about 1.4 MPa, as measured by the Extensional Test Method described herein.

The copolymer, as well as adhesive compositions comprising the copolymer, can have a Toughness at 37° C. of from about 2 $MJ/m^3$ to about 5 $MJ/m^3$, alternatively from about 2 $MJ/m^3$ to about 4 $MJ/m^3$, and alternatively from about 2.4 $MJ/m^3$ to about 4 $MJ/m^3$, as measured by the Extensional Test Method described herein.

Optional Ingredients

The adhesive composition described herein can comprise less than 10 wt. %, alternatively less than 5 wt. %, alternatively less than 3 wt. %, alternatively less than 2 wt. %, alternatively less than 1 wt. %, alternatively less than 0.5 wt. %, alternatively less than 0.3 wt. %, alternatively less than 0.2 wt. %, alternatively less than 0.1 wt. %, and alternatively less than 0.05 wt. % of one or more optional ingredients.

The adhesive composition can optionally include a plasticizer or plasticizing oil or extender oil that may reduce the viscosity or improve tack properties in the adhesive composition. Nonlimiting examples of plasticizers include olefin oligomers, low molecular weight polyolefins such as liquid polybutenes, low molecular weight non-aromatic polymers (e.g. REGALREZ 101 from Eastman Chemical Company), phthalates, mineral oils such as naphthenic, paraffinic, or hydrogenated (white) oils (e.g. Kaydol oil or ParaLux oils (Chevron U.S.A. Inc.)), vegetable and animal oils and their derivatives, petroleum derived oils, and combinations thereof. The plasticizers can include polypropylene, polybutene, hydrogenated polyisoprene, hydrogenated polybutadiene, polypiperylene, copolymers of piperylene and isoprene, as described in U.S. Pat. No. 8,865,824, which is expressly incorporated by reference.

The adhesive composition can optionally include an antioxidant or a stabilizer. Any antioxidant known to a person of ordinary skill in the art may be used in the adhesion composition. Non-limiting examples of suitable antioxidants include amine-based antioxidants such as alkyl diphenyl amines, phenyl-naphthylamine, alkyl or aralkyl substituted phenyl-naphthylamine, alkylated p-phenylene diamines, tetramethyl-diaminodiphenylamine and the like; and hindered phenol compounds such as 2,6-di-t-butyl-4-methylphenol; 1,3,5-trimethyl-2,4,6-tris(3',5'-di-t-butyl-4'-hydroxybenzyl)benzene; tetra kis [(methylene(3,5-di-t-butyl-4-hydroxyhydrocinnamate)]methane (e.g., IRGANOX™ 1010, from Ciba Geigy, New York); octadecyl-3,5-di-t-butyl-4-hydroxycinnamate (e.g., IRGANOX™ 1076, commercially available from Ciba Geigy) and combinations thereof. Where used, the amount of the antioxidant in the composition can be less than 1 wt. %, alternatively from about 0.05 wt. % to about 0.75 wt. %, and alternatively from about 0.1 wt. % to about 0.5 wt. % of the total weight of the adhesive composition.

The adhesive composition can optionally include a UV stabilizer that may prevent or reduce the degradation of the composition by radiation. Any UV stabilizer known to a person of ordinary skill in the art may be used in the adhesion composition. Non-limiting examples of suitable UV stabilizers include benzophenones, benzotriazoles, aryl esters, oxanilides, acrylic esters, formamidine carbon black, hindered amines, nickel quenchers, hindered amines, phenolic antioxidants, metallic salts, zinc compounds, and combinations thereof. Where used, the amount of the UV stabilizer in the adhesive composition can be less than 1 wt. %, alternatively from about 0.05 wt. % to about 0.75 wt. %, and alternatively from about 0.1 wt. % to about 0.5 wt. % of the total weight of the adhesive composition.

The adhesive composition can optionally include a brightener, colorant, and/or pigment. Any colorant or pigment known to a person of ordinary skill in the art may be used in the adhesive composition. Non-limiting examples of suitable brighteners, colorants, and/or pigments include fluorescent materials and pigments such as triazine-stilbene, coumarin, imidazole, diazole, titanium dioxide and carbon black, phthalocyanine pigments, and other organic pigments such as IRGAZINB, CROMOPHTALB, MONASTRALB, CINQUASIAB, IRGALITEB, ORASOLB, all of which are available from Ciba Specialty Chemicals, Tarrytown, N.Y. Where used, the amount of the brightener, colorant, and/or pigment in the adhesive composition can be less than 10 wt. %, alternatively from about 0.01 wt. % to about 5 wt. %, and alternatively from about 0.1 wt. % to about 2 wt. % of the total weight of the adhesive composition.

The adhesive composition can optionally include a fragrance such as a perfume or other odorant. Such fragrances may be retained by a liner or contained in release agents such as microcapsules that may, for example, release fragrance upon removal of a release liner from or compression on the adhesive composition.

The adhesive composition can optionally include a filler. Any filler known to a person of ordinary skill in the art may be used in the adhesive composition. Non-limiting examples of suitable fillers include sand, talc, dolomite, calcium carbonate, clay, silica, mica, wollastonite, feldspar, aluminum silicate, alumina, hydrated alumina, glass bead, glass microsphere, ceramic microsphere, thermoplastic microsphere, barite, wood flour, and combinations thereof. Where used, the amount of the filler in the adhesive composition can be less than 60 wt. %, alternatively from about 1 wt. % to about 50 wt. %, and alternatively from about 5 wt. % to about 40 wt. % of the total weight of the adhesive composition.

Applications

The adhesive compositions described herein have industrial applications in sanitary disposable consumer articles, for example, diapers, feminine care pads, and napkins. Articles can include items having any two or more substrates adhesively bonded by a hot melt adhesive composition, such as disposable articles such as diapers or feminine napkins. The substrates can include thermoplastics, thermoset polymers, polyesters, polyethylene terephthalate, polyamides, nylons, polypropylene, and combinations, blends, or layered composites thereof. The substrates can include, in some applications, coatings of wax, acrylate polymers, or other materials, colorants, preservatives, stabilizers, processing lubricants, and combinations thereof. The substrates can include solid, nonporous or breathable films. The substrates can include nonwoven fabrics and films (e.g., polyethylene films), in some applications.

The adhesive compositions can be used as a construction adhesive in assembly of commonly available consumer disposal articles. Such articles include infant diapers, adult diapers, bed pads, sanitary products, and other absorbent articles. Combining at least a polymer film with other films and fibrous materials typically makes these articles. Fibrous materials can include fabrics such as woven or nonwoven fabrics, fibers in the form of fiber vats, fiber collections, fiber balls, etc.

Such absorbent articles typically include an absorbent held within the article. The absorbent is usually covered using a nonwoven inner liner. Such liners include a highly permeable material such as a spun bonded nonwoven structure that passes fluids or moisture from the interior of the article into the absorbent layer. The absorbent layer or structure formed within the absorbent article typically includes a fiber mass pad or cellulosic or wood pulp for the purpose of absorbing liquid or fluid materials released into the absorbent article. The fiber or fluff can include a cellulosic fiber, a synthetic fiber or mixtures thereof such as blends of wood fiber, cellulosic fiber, polyethylene fiber, polypropene fiber or other fiber materials often including a super absorbent material. Super or highly absorbent materials are used to increase the absorptive capacity of the absorbent article. Such materials are organic materials including modified natural gums and resins but often include synthetic polymer materials such as hydrogels. Carboxymethyl cellulose, alkaline metal salts of acrylic polymers, polyacrylamides, polyvinyl alcohol, polyethylene anhydride polymers and copolymers, polyvinyl ether polymers and copolymers, hydroxyalkyl cellulose polymers and copolymers, polyvinyl sulfonic acid polymers and copolymers, polyacrylic polymers, polyvinyl-pyrrolidone polymers and copolymers can be used in the absorbent function.

Nonwoven fabric layers used in such disposal articles typically are generally planar structures including a bonded assembly of natural or synthetic fiber.

Such nonwoven materials are often made using a variety of techniques, including spun bonding, melt bonding, etc. Such nonwoven materials are often manufactured by randomly placing fibers or rovings in a random pattern and are then thermally bonded using inherent bonding characteristics of the fibers or by bonding the fibers using resin materials applied to the fibers. Various polymers can be used to make nonwoven materials including poly olefins, polyesters, ethylene vinyl acetate polymers, ethylene acrylic acid polymers and others.

The exterior of the article often includes a polymer film that is liquid impervious. In certain aspects exterior polymer films can be further modified using additional exterior layers to obtain a more cloth like or nonwoven character to the exterior polymer film. The exterior film typically includes a single layer of a polymer film but can be a multi-layer film structure. Typical polymer sheet materials include high tensile strength polymers including polyesters, poly olefins or other thermoplastic sheet materials that can be formed into film layers. The polyolefin or polyester polymer materials are often formed into sheets and are treated to improve strength, flexibility and puncture resistance. Techniques including biaxial orientation, heat treatment or surface treatment can improve the film characteristics of the polymer films. Such polymer films often have a thickness that ranges from about 0.5 mils (i.e., one thousandth of an inch) to about 1.5 mils.

The absorbent articles can include a liquid impervious polymer film, an absorbent layer pad and a nonwoven interior layer. A three component structure can be assembled using the adhesive composition that is applied using manufacturing techniques that adheres the nonwoven interior layer to the polymer film while holding the absorbent layer there between.

Methods of manufacture employing the adhesive compositions include the application of the molten adhesive compositions to a substrate, followed by contact of the adhesive composition with a second substrate within 0.1 second to 5 seconds after application of the adhesive composition to the first substrate, wherein the contacting results in an adhesive bond between the substrates.

In the articles manufactured using the adhesive compositions, the articles can be manufactured by forming an adhesive bond between a polymer film and a fiber or fiber mass. The article can also include an adhesive bond formed between a polymer film and a nonwoven fabric. Additionally the article can be manufactured by forming an adhesive bond between a multi-layer structure including the exterior layer of a polymer film and interior components including a fiber map or a nonwoven fabric.

The adhesive compositions can be applied under melt conditions to a substrate as a hot melt adhesive or may be coated, applied or sprayed onto the polymer film nonwoven or absorbent pad. Spray-on adhesives are typically applied using slot coat, spray on or atomizing character in a bead, dot pattern, spiral pattern or other conventional pattern using such Nordson application techniques. The adhesive composition can be applied to a substrate using a slot coat (using Nordson true coat or Speed coat slot) at increased machine speed.

The adhesive composition can be applied in an amount of about 1 to about 25 grams per square meter ($g\text{-}m^{-2}$) of resulting bonded material. The adhesive composition can be used for disposal diaper and napkin construction elastic attachment and disposal goods particularly preferred applications include baby diaper construction, diaper chassis construction, diaper core stabilization, diaper outer cover lamination, feminine napkin core stabilization, and feminine napkin construction bond.

Test Methods

Static Peel Time Test Method

The Static Peel Time of a hot melt adhesive composition is determined by using the Static Peel Time Test Method, which consists of first using the hot melt to create a bond between two specified substrates using a specified slot coating process to form a laminate, as described below. Specimens extracted from the substrates are then subjected to a 180-degree peel test under static load, and the average time to failure is reported as the "Static Peel Time."

Preparation of Laminate

Two specified substrates are affixed via a specified slot coating process using the hot melt adhesive composition to form a laminate. The first substrate used to form the laminate, the "nonwoven," is a 15 gsm polypropylene spunbond (SSS) with a point bond pattern (diamonds, 0.87 mm$^2$ per point bond) that covers 18.6% bond area and has 21.5 points per square centimeter. The average fiber diameter is 17 microns. The nonwoven is provided in roll stock form and is 212 mm in width. The second substrate used to form the laminate, the "film," is a microporous polyethylene film with basis weight of 16 gsm. The average print coverage area is 16.7%. Exemplary suitable films are MICROPRO microporous films, and films designated BR137P and BR137U, available from Clopay (Clopay Plastics Corporation, Mason, OH, USA), or equivalent. The film is provided in roll stock and is 206 mm in width.

The hot melt adhesive composition is slot coated onto the moving nonwoven web. The nonwoven web-speed is 573 m/min and the total nonwoven web tension at the point of application is 0.5 lbs (10.5 N/m tension per unit width). The adhesive is slot coated onto the nonwoven using a True-Coat™ die from Nordson (Nordson LU12K04139/8138208, Nordson Corporation, Westlake, OH, USA, or equivalent).

The shim of the die is 0.3 mm thick and cut with an alternating pattern to create 60 openings, each 1 mm wide, with 1 mm wide spacings between each opening. This creates a coating of 60 continuous stripes of adhesive in the machine direction, each stripe of adhesive is 1 mm wide with a 1 mm uncoated spacing between adhesive stripes. The adhesive flow rate for the nozzle is set such that the basis weight of each adhesive stripe is 2.2±0.1 gsm. The adhesive is maintained at a temperature of 150±5° C. at all points up to and including the applicator. This overall slot coating process is performed at an ambient temperature of 21±2° C.

The adhesive is applied to the nonwoven web with the slot coat die by bringing the slot coat die into contact with the nonwoven supported between two non-driven web-support idlers that co-rotate with the moving nonwoven web and each have 57 mm diameter. The spacing of the web-support idlers is set to 155 mm, center to center, and the adhesive applicator's exit is set at a point 7 mm from the downstream idler's center. The applicator is pressed into the nonwoven between the idlers, such that the nonwoven is deflected 3-4 mm at the exit point of the adhesive from the slot coat die, with respect to the plane made by the nonwoven under tension when the applicator is absent. The angle made between the slot coat die's shim plane and the plane of the tensioned nonwoven when the applicator is not engaged, is the pitch angle. This angle is described to be zero when the planes are perpendicular to each other. For the laminates, the adhesive was coated with a positive 3° pitch angle towards the downstream idler. In other words, the plane of the shim relative to the plane of the tensioned nonwoven when the applicator is not engaged, is 87° on the side of the downstream idler. The adhesive coating is centered along the length of the nonwoven web by centering the width of the slot coat die on the width of the nonwoven.

The adhesive coated nonwoven web is then brought into contact with the film about 970 mm after coating. The web speed of the film is 573 m/min, and the total film's web tension is 1.0 lb (21 N/m, tension per unit width). The contact point between the two webs is made at a 57 mm diameter idler and the webs are wrapped around the idler with a 190° wrap angle. The combined web is wound on a roll with 1.5 lbs winding tension and samples are immediately cut off the roll after winding. The removed samples are allowed to equilibrate at 21±2° C. and 40% relative humidity for a minimum of 20 hours before static peel testing.

Peel Under Static Load

Specimens are removed at random from the equilibrated laminate. Specimens measure 40 mm in the machine direction of the laminate and across the entire cross direction of the laminate such that all sixty 1-mm wide stripes of slot-coated hot melt adhesive composition are included in the cross machine length of the strip.

The static peel is conducted in a direction transverse to the machine direction (e.g., perpendicular to the adhesive stripe direction). On one 40 mm wide edge of the laminate test specimen, each unbonded layer at the edge of the laminate is separately folded over a small round wooden dowel rod 2 mm in diameter and approximately 40 mm long, and the wrapped dowels are secured with a 2 inch wide bulldog clip. The clip is placed over the wrapped dowel and clamped onto the doubled layer of material such that the material does not slip or pull out of the clip. With clips attached, the test specimens are placed in preconditioned incubator (at 37±1° C.) for about 10 minutes before testing. After 10 minutes, each sample is suspended in the chamber by the clip attached to the film layer, and a weight is attached to the nonwoven's clip, hanging therefrom. The hanging weight, the bulldog clip, and the dowel have a total weight of 25 grams. The specimen is suspended such that the bottom of the attached weight is located high enough above the bottom of the chamber so that the entire laminate can peel apart and the weight can freely fall to the bottom of the chamber through some remaining distance. A timer is used to measure the time between the time at which the hanging weight is attached and the time at which the bonded area of the test laminate fully delaminates. For each specimen, this time to failure is recorded to the nearest second. The peel under static load is performed on at least ten specimens, and the arithmetic mean of the time to failure is defined as the "Static Peel Time," reported to the nearest second.

Needle Penetration Test Method

The Needle Penetration of a hot melt adhesive composition is determined using the Needle Penetration Test Method, which consists of performing ASTM D5/D5M-13 with a Humboldt H1280 needle and the following additional guidance. Ambient temperature is maintained at 21.5±1.0° C., and specimen(s) of hot melt adhesive composition to be tested are thermally equilibrated prior to measurement. A total load of 100 g as described in section 6 of ASTM D5/D5M-13 is used, and the allowed penetration time is 5.0±0.2 seconds. The arithmetic mean of the distance of needle penetration for three replicates, as described in section 10 of ASTM D5/D5M-13, is defined as the "Needle Penetration" and is reported in units of tenths of a millimeter (that is, decimillimeters, or dmm) to the nearest whole value in dmm.

Tensile Strength Test Method

The Tensile Strength of a hot melt adhesive composition is determined using the Tensile Strength Test Method, which consists of performing ASTM D638-14 with the following additional guidance. Ambient temperature is maintained at 23.0±1.0° C. Hot melt adhesive composition is cast into a shape consistent with a Type IV "dogbone" as described in FIG. 1 of ASTM D638-14 and allowed to equilibrate to ambient temperature. The test proceeds with a crosshead speed of 50 mm/min. Tensile Strength at Yield is calculated as described in section 11.2 of ASTM D638-14 and is reported as the "Tensile Strength at Yield" in units of megapascals (MPa) to the nearest 0.01 MPa.

Viscosity Test Method

The Viscosity Parameter of a hot melt adhesive composition is determined using the Viscosity Parameter Test Method, which consists of performing ASTM D3236-15 with the following additional guidance. A Brookfield RVT viscometer with spindle SC 4-27 (Brookfield Engineering, Middleboro, MA, USA), or equivalent, is used. The sample temperature is maintained at 150.0±1.0° C. is throughout the measurement. The sample is preheated for 10 minutes and stirred with the measurement spindle for 30 min. The spindle is rotated at 20 rpm throughout the measurement. The resulting apparent viscosity, as described in section 10, is reported as the "viscosity" in units of millipascal-seconds to the nearest 100 mPa·s.

Mettler Cup and Ball Test Method

The Mettler Cup and Ball Parameter is determined using the Mettler Cup and Ball Test Method, which consists of performing ASTM D3461-14 with a heating rate of heating is 2° C./min. The softening point as defined in ASTM D3461-14 is recorded and reported to the nearest 0.1° C. as the Mettler Cup and Ball Parameter.

Enthalpy of Fusion Test Method

The Enthalpy of Fusion Parameter of a hot melt adhesive composition is determined using the Enthalpy of Fusion Test Method, which consists of performing ASTM D3418-15 with the following additional guidance. Specimen(s) are preferably extracted from molded or pelleted raw material adhesive composition. If raw material is not available, specimen(s) of adhesive are extracted from bonds of interest in an absorbent article using techniques known to those of skill in the art. Dry nitrogen is used as the purge gas in the differential scanning calorimeter (DSC). The rate of increase of temperature in the DSC is 10° C./min, and the rate of decrease of temperature in the DSC is 1° C./min. The mass-normalized enthalpy of fusion is calculated as specified in section 11.4 based on the curve corresponding to decreasing temperature (at 1° C./min) and is reported as the "Enthalpy of Fusion" in units of joules per gram (J/g) to the nearest 0.1 J/g.

Oscillatory Rheometry Test Method

The Oscillatory Rheometry Test Method is used to measure the Storage Modulus and the Loss Factor of a hot melt adhesive composition. A controlled-stress rotational rheometer (such as Discovery HR-3, TA Instruments, New Castle, DE, USA, or equivalent) capable of sample temperature control (using a Peltier cooler and resistance heater combination) with a precision equal to or exceeding 0.5° C. over at least the range of −10° C. to 150° C. The rheometer is operated in a parallel plate configuration with 20-mm stainless steel parallel-plate tooling.

A parallel plate gap of 1000 μm is initially used in the method. To compensate for thermal expansion of the tooling, the gap is set to 1000 μm, and a mapping of actual plate gap (as measured using a suitable standard test fluid) a function of temperature over the range −10° C. to 150° C. is performed. This mapping is then used throughout the determination of the Storage Modulus Parameter and the Loss Factor Parameter.

The rheometer is heated to 150° C., hot melt adhesive composition is introduced in the rheometer, the gap is set to 1050 μm, excess protruding sample is trimmed, and the gap is then set to 1000 μm. (The axial force control of the rheometer is set to be maintained within ±0.1 N of force, and the thermal expansion/contraction of the sample itself is compensated in order to avoid overfilling or underfilling of the gap in addition to the abovementioned compensation of the tooling.) The rheometer is then allowed to cool to 130° C., at which point the measurement commences with temperature ramped from 130° C. to −10° C. at a constant rate of cooling of 2° C./min. The applied strain amplitude is 0.1%, and the frequency of oscillation is 1 Hz (that is, one cycle per second). The resulting oscillatory stress is recorded.

After this step, the sample temperature is set to 23° C. (temperature is ramped to this setpoint at a rate of 10° C./min), and the sample is allowed to rest for 4.0 hours at 23° C. At the end of this period, the temperature is set to −10° C. (temperature is ramped to this setpoint at a rate of 10° C./min), the sample is equilibrated for 300 seconds at −10° C., and a second oscillatory rheology measurement is conducted (0.1% strain, frequency of oscillation of 1 Hz) while temperature is ramped upward to 130° C. at a constant rate of increase of 2° C./min.

From the second, increasing temperature sweep, the storage modulus G' is calculated and recorded at 23° C. and 37° C., and these values are reported in megapascals (MPa) to the nearest 0.01 MPa as the "Storage Modulus at 23° C." and the "Storage Modulus at 37° C.," respectively. From the second, increasing temperature sweep, the loss factor (also known as tan delta) is calculated recorded at 23° C. and 37° C., and these dimensionless values are reported to the nearest hundredth as the "Loss Factor at 23° C." and the "Loss Factor at 37° C.," respectively.

Extensional Test Method

The Extensional Test Method is used to determine the Yield Stress and the Toughness for a specimen of an adhesive composition. A thin film specimen formed of adhesive composition is analyzed with a rotational rheometer fitted with a specialized fixture with counter rotating rollers, and the stress associated with extensional strain imparted is measured and recorded.

Instrumental Setup

A rotational rheometer (ARES G2, TA Instruments, New Castle, DE, USA, or equivalent) is fitted with a fixture that has counter rotating cylindrical rollers specifically designed for the interrogation of extension deformation of films. An example of a suitable fixture is the Extensional Viscosity Fixture, or EVF (EVF, TA Instruments, or equivalent). The rheometer is further fitted with a forced-convection oven FCO (FCO, TA Instruments, or equivalent) and cooling system (ACS 2, TA Instruments, or equivalent) capable of controlling temperate from at least −50 to 250° C. to a within a tolerance of 0.5° C.

Specimen Preparation

Approximately 10 g of the adhesive composition is placed in a polytetrafluoroethane (PTFE) bowl and introduced into a vacuum oven. After 15 minutes at 170° C. at ambient pressure, the pressure is lowered to 10 mbar, and the adhesive composition is subsequently held at 170° C. and at 10 mbar for 45 minutes to remove air bubbles from the adhesive composition. The adhesive composition is removed from the vacuum oven and allowed to cool to ambient lab conditions (23±2° C.) for 90±30 minutes, at which point the adhesive composition is removed from the PTFE bowl and placed between 2 sheets of siliconised paper. A metal shim 0.50 mm in thickness is used in the heated press as a spacer to obtain a film thickness of 0.50 mm when pressed with a heated press at 90° C. for 60 seconds at a pressure sufficient to form a polymeric film. If 90° C. is insufficient to melt the adhesive composition, a higher temperature (but the lowest temperature sufficient to melt the composition) is used. The film is stored at least 120 hours in the laboratory at 23±2° C. prior to testing. From the film individual specimens for measurement are punched with a sample cutter to the final specimen dimensions of 20.0 mm by 10.0 mm by 0.50 mm.

Measurement

The cylinders of the EVF are heated to 50° C. for 90±30 s in the forced-convection oven of the rheometer. A specimen of adhesive composition is quickly pressed onto the cylinders of the EVF to fix it to the cylinder surface. The specimen is placed perpendicular to the axis of rotation of the cylinders.

The specimen mounted on the EVF is then placed in the forced convection oven of the rheometer for thermal conditioning and is kept isothermal at 37±1° C. for 300±10 s. After this time has elapsed, the specimen is mechanically conditioned. To mechanically condition the specimen, the torque transducer is zeroed, and the sample is put under a pre-stretch rate of 0.001 $s^{-1}$ for 0.30 s and then allowed to relax for 60 s. (In this method, all strain is expressed in terms of Hencky strain, also known as "true strain" or "logarithmic strain.")

The measurement is performed in the FCO oven at 37° C.±0.5° C. The strain rate extension for the measurement is 1 $s^{-1}$, and the strain at maximum extension is 4.0. After measurement, the specimen is checked for rupturing. If it has ruptured, the location of the break is noted. If the rupture is approximately in the middle between the two cylinders of the EVF, the data collected are deemed acceptable. Otherwise, if the polymeric film break is at or close to the rotating cylinders, the results are discarded and the measurement performed again on a replicate specimen.

Analysis

For the extensional stress calculation, a constant volume is assumed. From the raw torque versus angular displacement data recorded by the rheometer, extensional stress (in megapascals, or MPa) versus Hencky strain data are calculated. The data are plotted in semilogarithmic fashion with Hencky strain on the abscissa (linear scale) and extensional stress on the ordinate (logarithmic scale). A linear range is sought in this plot. If a linear range can be identified and this range can be fit with a positive slope with an $R^2$ value of 0.98 or greater, the value of the fitted line at a Hencky strain of zero (that is, the y-intercept), is defined as the Yield Stress, which is reported in Mpa to the nearest kilopascal. Otherwise, the maximum value of extensional stress recorded during the measurement is reported as the Yield Stress, again reported in Mpa to the nearest kilopascal.

The extensional stress (MPa) versus Hencky strain data calculated above are again plotted, but this time in linear fashion with Hencky strain on the abscissa (linear axis) and extensional stress on the ordinate (linear axis). The integral of extensional stress with strain (that is, the area under the extensional stress curve as a function of strain) is calculated from a strain of zero to the strain at which the sample ruptured (or, in the case it did not rupture during the measurement, to a strain of 4.0) and is reported as the Toughness, which is reported in units of megajoules per cubic meter, or $MJ\ m^{-3}$.

EXAMPLES

The following examples are provided to help illustrate the adhesive composition herein. The exemplified adhesive compositions may be prepared by conventional formulation and mixing techniques. It will be appreciated that other modifications of the adhesive compositions described herein within the skill of those in the formulation art may be undertaken. All parts, percentages, and ratios herein are by weight unless otherwise specified. Some components may come from suppliers as dilute solutions. The amount stated reflects the weight percent of the active material, unless otherwise specified.

Table 1 provides exemplary adhesive compositions, wherein descriptions of the components and amount ranges of the components are shown. Copolymer A, B, C and D are amorphous copolymers of 1-butene monomer units and propene monomer units. Heterophase Copolymer A and Heterophase Copolymer B are heterophase copolymers of ethylene monomer units and propene monomer units.

TABLE 1

| Component | Adhesive Composition A Wt. % | Adhesive Composition B Wt. % | Adhesive Composition C Wt. % |
|---|---|---|---|
| Copolymer A (REXtac RT2715) | 20 | — | 50 |
| Copolymer B (ex. REXtac) | 60 | — | — |
| Copolymer C (ex. REXtac) | — | 65 | — |
| Copolymer D (REXtac RT2788) | — | — | 30 |
| Heterophase Copolymer A (Clariant Licocene PP2502) | 10 | — | — |
| Heterophase Copolymer B (Clariant Licocene PP1302) | 10 | 35 | 20 |

Table 2 shows exemplary and comparative adhesive compositions.

TABLE 2

| | Melt Viscosity @ 150° C. (mPa · s) | Enthalpy of Fusion (J/g) | Static Peel Test Performance (seconds) | Tensile Strength at Yield (MPa) | Spray Pattern |
|---|---|---|---|---|---|
| Adhesive Composition A | 3600 | 14.0 | 395 | 1.28 | Acceptable |
| Adhesive Composition B | 4000 | 8.7 | 426 | 1.08 | Acceptable |
| Adhesive Composition C | 5475 | 12.8 | 483 | 0.93 | Acceptable |
| Copolymer A (REXtac RT2715) | 3900 | 5.2 | 135 | 0.28 | Unacceptable |
| Copolymer E (REXtac RT2730) | 8200 | 6.0 | 214 | 0.31 | Unacceptable |
| Copolymer F (REXtac RT2830) | 8200 | 19.7 | 52 | 2.41 | Unacceptable |

During some testing, less than 1% of antioxidants and other minor ingredients were added for preservation and packaging purposes, but it is believed that the 1% of antioxidants and the other minor ingredients had no effect on the provided data in Table 2.

The spray pattern is assessed using the method disclosed in US 20040081795 A1, which is incorporated herein in its entirety. In US 20040081795 A1, the spray pattern was deemed acceptable if a good spiral pattern as that depicted in FIG. 1b was observed; otherwise, it was deemed unacceptable (FIG. 1a).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any application disclosed or claimed herein or that it alone, or in any combination with any other reference or references, teaches, suggests or discloses any such application. Further, to the extent that any meaning or definition of a term in this document conflicts with any meaning or definition of the same term in a document incorporated by reference, the meaning or definition assigned to that term in this document shall govern.

While particular embodiments of the adhesive composition have been illustrated and described, it would be obvious to those skilled in the art that various other changes and modifications may be made without departing from the spirit and scope of this document. It is therefore intended to cover in the appended claims all such changes and modifications that are within the scope of this document.

What is claimed is:

1. An absorbent article having a longitudinal centerline and a lateral centerline, a front waist region with a front waist edge, a rear waist region with a rear waist edge, a crotch region disposed between the front waist region and the rear waist region, and two spaced apart longitudinal side edges joining the front waist edge to the rear waist edge, wherein the absorbent article comprises an assembly of components, and wherein the assembly of components comprises:
   a) a topsheet;
   b) a backsheet underlying the topsheet;
   c) an absorbent core disposed between the topsheet and the backsheet, wherein the absorbent core comprises at least one of a core cover, a dusting layer, an acquisition layer, a distribution layer, and a storage member;
   d) at least one additional component selected from the group consisting of:
      i) a fastening system for joining the front waist region to the rear waist region when the absorbent article is worn;
      ii) barrier cuffs lying adjacent and inboard the two spaced apart longitudinal side edges;
      iii) gasketing cuffs lying between each of the two spaced apart longitudinal side edges and the barrier cuffs;
      iv) front ears disposed in the front waist region;
      v) back ears disposed in the rear waist region; and
      vi) a receiving member; and
   e) a spray-on adhesive composition joining at least two of the assembly of components together, wherein the spray-on adhesive composition comprises:
      i) from about 50 wt. % to about 80 wt. % of one or more copolymers, wherein each of the one or more copolymers comprise from about 30 mole % to about 70 mole % of monomer units selected from the group consisting of ethylene, 1-butene, and mixtures thereof; and wherein the one or more copolymers comprise from about 30 mole % to about 70 mole % of propene monomer units; and
      ii) a blend of heterophase copolymers; wherein the blend of heterophase copolymers comprises from about 70 wt. % to about 99.5 wt. % of a first heterophase copolymer and from about 0.1 wt. % to about 30 wt. % of a second heterophase copolymer; and
   wherein the first heterophase copolymer has a higher Enthalpy of Fusion than the second heterophase copolymer, as measured by the Enthalpy of Fusion Test Method;
   wherein the spray-on adhesive composition is free of polyisobutylene;
   wherein the spray-on adhesive composition has a viscosity of from about 2,000 mPa·s to about 11,500 mPa·s at 150° C., as measured by the Viscosity Test Method.

2. The absorbent article of claim 1, wherein the spray-on adhesive composition joins the topsheet to an underlying nonwoven layer.

3. The absorbent article of claim 1, wherein the spray-on adhesive composition joins the topsheet to the backsheet adjacent one of the two spaced apart longitudinal side edges.

4. The absorbent article of claim 1, wherein the spray-on adhesive composition joins the core cover to the dusting layer.

5. The absorbent article of claim 1, wherein the spray-on adhesive composition joins the dusting layer to the backsheet.

6. The absorbent article of claim 1, wherein the spray-on adhesive composition has an Enthalpy of Fusion of less than 15 J/g.

7. The absorbent article of claim 1, wherein the spray-on adhesive composition has a density of from about 0.5 g/cm$^3$ to 0.85 g/cm$^3$ at 150° C.

8. The absorbent article of claim 1, wherein the plurality of copolymers comprise a first copolymer and a second copolymer, and wherein the spray-on adhesive composition comprises from about 35 wt. % to about 80 wt. % of the first copolymer and from about 10 wt. % to about 35 wt. % of the second copolymer.

9. The absorbent article of claim 1, wherein the spray-on adhesive composition comprises less than 20 wt. % of a tackifier.

10. An absorbent article having a longitudinal centerline and a lateral centerline, a front waist region with a front waist edge, a rear waist region with a rear waist edge, a crotch region disposed between the front waist region and the rear waist region, and two spaced apart longitudinal side edges joining the front waist edge to the rear waist edge, wherein the absorbent article comprises an assembly of components, and wherein the assembly of components comprises:
   a) a topsheet;
   b) a backsheet underlying the topsheet;
   c) an absorbent core disposed between the topsheet and the backsheet, wherein the absorbent core comprises at least one of a core cover, a dusting layer, an acquisition layer, a distribution layer, and a storage member;
   d) at least one additional component selected from the group consisting of:
      i) a fastening system for joining the front waist region to the rear waist region when the absorbent article is worn;
      ii) barrier cuffs lying adjacent and inboard the two spaced apart longitudinal side edges;

iii) gasketing cuffs lying between each of the two spaced apart longitudinal side edges and the barrier cuffs;
iv) front ears disposed in the front waist region;
v) back ears disposed in the rear waist region; and
vi) a receiving member; and e) a spray-on adhesive composition joining at least two of the assembly of components together, wherein the spray-on adhesive composition comprises:
  i) from about 50 wt. % to about 80 wt. % of a plurality of copolymers, wherein each of the plurality of copolymers comprise from about 30 mole % to about 70 mole % of monomer units selected from the group consisting of ethylene, 1-butene, and mixtures thereof; and wherein the plurality of copolymers comprise from about 30 mole % to about 70 mole % of propene monomer units; and
  ii) a blend of heterophase copolymers; wherein the blend of heterophase copolymers comprises from about 70 wt. % to about 99.5 wt. % of a first heterophase copolymer and from about 0.1 wt. % to about 30 wt. % of a second heterophase copolymer;
  wherein the spray-on adhesive composition is free of polyisobutylene;
  wherein the spray-on adhesive composition has a viscosity of from about 2,000 mPa·s to about 11,500 mPa·s at 150° C., as measured by the Viscosity Test Method;
  wherein the spray-on adhesive composition has an Enthalpy of Fusion of less than 15 J/g, as measured by the Enthalpy of Fusion Test Method; and
  wherein the plurality of copolymers comprises a first copolymer and a second copolymer, and wherein the spray-on adhesive composition comprises from about 40 wt. % to about 75 wt. % of the first copolymer and from about 5 wt. % to about 40 wt. % of the second copolymer.

11. The absorbent article of claim 10, wherein the spray-on adhesive composition joins the topsheet to an underlying nonwoven layer.

12. The absorbent article of claim 10, wherein the spray-on adhesive composition joins the topsheet to the backsheet adjacent one of the two spaced apart longitudinal side edges.

13. The absorbent article of claim 10, wherein the spray-on adhesive composition joins the core cover to the dusting layer.

14. The absorbent article of claim 10, wherein the spray-on adhesive composition joins the dusting layer to the backsheet.

15. The absorbent article of claim 10, wherein the plurality of copolymers comprise from about 30 wt. % to about 70 wt. % 1-butene monomer units.

16. The absorbent article of claim 10, wherein the spray-on adhesive composition comprises less than 20 wt. % of a tackifier.

17. The absorbent article of claim 10, wherein the spray-on adhesive composition has a density of from about 0.5 g/cm³ to 0.85 g/cm³ at 150° C.

18. An absorbent article having a longitudinal centerline and a lateral centerline, a front waist region with a front waist edge, a rear waist region with a rear waist edge, a crotch region disposed between the front waist region and the rear waist region, and two spaced apart longitudinal side edges joining the front waist edge to the rear waist edge, wherein the absorbent article comprises an assembly of components, and wherein the assembly of components comprises:
a) a topsheet;
b) a backsheet underlying the topsheet;
c) an absorbent core disposed between the topsheet and the backsheet, wherein the absorbent core comprises at least one of a core cover, a dusting layer, an acquisition layer, a distribution layer, and a storage member;
d) at least one additional component selected from the group consisting of:
  i) a fastening system for joining the front waist region to the rear waist region when the absorbent article is worn;
  ii) barrier cuffs lying adjacent and inboard the two spaced apart longitudinal side edges;
  iii) gasketing cuffs lying between each of the two spaced apart longitudinal side edges and the barrier cuffs;
  iv) front ears disposed in the front waist region;
  v) back ears disposed in the rear waist region; and
  vi) a receiving member; and
e) a spray-on adhesive composition joining at least two of the assembly of components together, wherein the spray-on adhesive composition comprises:
  i) from about 50 wt. % to about 80 wt. % of a plurality of copolymers, wherein each of the plurality of copolymers comprise (i) from about 30 mole % to about 70 mole % of 1-butene monomer units; and (ii) from about 30 mole % to about 70 mole % of propene monomer units; and
  ii) a blend of heterophase copolymers; wherein the blend of heterophase copolymers comprises from about 70 wt. % to about 99.5 wt. % of a first heterophase copolymer and from about 0.1 wt. % to about 30 wt. % of a second heterophase copolymer;
  wherein the spray-on adhesive composition is free of polyisobutylene;
  wherein the spray-on adhesive composition has a viscosity of from about 2,000 mPa·s to about 11,500 mPa·s at 150° C., as measured by the Viscosity Test Method;
  wherein the spray-on adhesive composition has an Enthalpy of Fusion of less than 15 J/g, according to the Enthalpy of Fusion Test Method; and
  wherein the plurality of copolymers comprises a first copolymer and a second copolymer, and wherein the spray-on adhesive composition comprises from about 35 wt. % to about 80 wt. % of the first copolymer and from about 10 wt. % to about 35 wt. % of the second copolymer.

19. The absorbent article of claim 18, wherein the spray-on adhesive composition joins the topsheet to an underlying nonwoven layer.

20. The absorbent article of claim 18, wherein the spray-on adhesive composition joins the topsheet to the backsheet adjacent one of the two spaced apart longitudinal side edges.

* * * * *